US011033543B2

(12) United States Patent
Dunayevich et al.

(10) Patent No.: US 11,033,543 B2
(45) Date of Patent: *Jun. 15, 2021

(54) METHODS OF PROVIDING WEIGHT LOSS THERAPY IN PATIENTS WITH MAJOR DEPRESSION

(71) Applicant: Nalpropion Pharmaceuticals, LLC, Morristown, NJ (US)

(72) Inventors: Eduardo Dunayevich, Westlake Village, CA (US); Gary Tollefson, Indianapolis, IN (US)

(73) Assignee: Nalpropion Pharmaceuticals LLC, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/441,863

(22) Filed: Jun. 14, 2019

(65) Prior Publication Data
US 2019/0290640 A1    Sep. 26, 2019

Related U.S. Application Data

(63) Continuation of application No. 15/011,120, filed on Jan. 29, 2016, now Pat. No. 10,322,121, which is a continuation of application No. 12/987,909, filed on Jan. 10, 2011, now Pat. No. 9,248,123.

(60) Provisional application No. 61/293,844, filed on Jan. 11, 2010.

(51) Int. Cl.
A61K 31/485    (2006.01)
A61P 3/04      (2006.01)
A61K 31/137    (2006.01)
A61K 31/439    (2006.01)
A61K 9/00      (2006.01)

(52) U.S. Cl.
CPC .......... *A61K 31/485* (2013.01); *A61K 9/0053* (2013.01); *A61K 31/137* (2013.01); *A61K 31/439* (2013.01); *A61P 3/04* (2018.01); *Y10S 514/909* (2013.01); *Y10S 514/91* (2013.01)

(58) Field of Classification Search
None
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,828,836 A | 5/1989 | Elger et al. |
| 4,831,031 A | 5/1989 | Lowe et al. |
| 4,855,306 A | 8/1989 | Markstein et al. |
| 4,895,845 A | 1/1990 | Seed |
| 5,000,886 A | 3/1991 | Lawter et al. |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |

(Continued)

OTHER PUBLICATIONS

Hausenloy, "Contrave: novel treatment for obesity", 2009, Clinical Lipidology, vol. 4(3), pp. 279-285.*

Klein et al., "Naltrexone+Bupropion Combination Causes Significant Weight Loss without Worsening Psychiatric Symptoms", Jun. 1, 2009, Diabetes, vol. 58(Suppl. 1), p. A444, Abstract. 1730-P.*

Bradley, Paul S., et al., "Bupropion SR Versus Placebo: Comparison of Depressive Symptoms and Weight Loss in Obese Patients with a History of Major Depression", International Journal of Obesity, Newman Publishing, London, GB, vol. 26, No. Suppl. 1, (Aug. 2002), p. S156 Abstract 592.

(Continued)

*Primary Examiner* — Savitha M Rao
*Assistant Examiner* — Gregg Polansky
(74) *Attorney, Agent, or Firm* — Servilla Whitney LLC

(57) ABSTRACT

Disclosed are methods of providing weight loss therapy, particularly for patients suffering from major depression.

19 Claims, No Drawings

(56) References Cited

U.S. PATENT DOCUMENTS

| | | |
|---|---|---|
| 6,087,386 A | 7/2000 | Chen et al. |
| 6,096,341 A | 8/2000 | Seth |
| 6,110,973 A | 8/2000 | Young |
| 6,120,803 A | 9/2000 | Wong et al. |
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,541,478 B1 | 1/2003 | O'Malley et al. |
| 6,514,531 B1 | 2/2003 | Alaux et al. |
| 6,528,520 B2 | 3/2003 | Clemens |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,088,786 B2 | 1/2012 | McKinney et al. |
| 8,318,788 B2 | 11/2012 | McKinney et al. |
| 8,722,085 B2 | 5/2014 | McKinney et al. |
| 8,815,889 B2 | 8/2014 | Cowley et al. |
| 8,916,195 B2 | 12/2014 | McKinney et al. |
| 8,969,371 B1 | 3/2015 | Klassen et al. |
| 9,107,837 B2 | 8/2015 | McKinney |
| 9,119,850 B2 | 9/2015 | Klassen et al. |
| 9,125,868 B2 | 9/2015 | McKinney et al. |
| 9,248,123 B2 | 2/2016 | Dunayevich et al. |
| 9,457,005 B2 | 10/2016 | Cowley et al. |
| 10,322,121 B2 * | 6/2019 | Dunayevich |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hintz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0132850 A1 | 9/2002 | Bartholomaeus et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Anderson et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026966 A1 | 2/2005 | Maruani et al. |
| 2005/0026977 A1 | 2/2005 | Jennings |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0169990 A1 | 8/2005 | Kao et al. |
| 2005/0181049 A1 | 8/2005 | Dong et al. |
| 2005/0214368 A1 | 9/2005 | Kawakami et al. |

(56) References Cited

U.S. PATENT DOCUMENTS

| | | |
|---|---|---|
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2007/0281021 A1* | 12/2007 | McKinney |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2012/0010232 A1 | 1/2012 | Weber et al. |
| 2013/0177602 A1 | 7/2013 | McKinney et al. |
| 2013/0245056 A1 | 9/2013 | Flanagan |
| 2013/0252995 A1 | 9/2013 | Dunayevich et al. |
| 2014/0080857 A1 | 3/2014 | McKinney et al. |
| 2014/0364468 A1 | 12/2014 | Gadde et al. |
| 2015/0119417 A1 | 4/2015 | Tollefson |
| 2015/0141452 A1 | 5/2015 | Weber et al. |
| 2015/0164806 A1 | 6/2015 | McKinney et al. |
| 2015/0182524 A1 | 7/2015 | Klassen et al. |
| 2015/0366860 A1 | 12/2015 | Klassen et al. |
| 2016/0158221 A1 | 6/2016 | McKinney et al. |
| 2016/0158225 A1 | 6/2016 | McKinney et al. |
| 2016/0193152 A1 | 7/2016 | McKinney et al. |
| 2016/0310485 A1 | 10/2016 | Klassen et al. |
| 2016/0338965 A1 | 11/2016 | McKinney et al. |
| 2016/0354346 A1 | 12/2016 | McKinney et al. |
| 2017/0007598 A1 | 1/2017 | Weber et al. |
| 2017/0014404 A1 | 1/2017 | McKinney et al. |
| 2017/0020990 A1 | 1/2017 | Cowley et al. |

OTHER PUBLICATIONS

Schneider, Kristin L., et al., "Design and Methods for a Randomized Clinical Trial Treating Comorbid Obesity and Major Depressive Disorder", BMC Psychiatry, BioMed Central, London, GB, (Sep. 2008), vol. 8, No. 1, p. 77 11 pages.

Dannon, Pinhas N., et al., "Sustained-release Bupropion Versus Naltrexone in the Treatment of Pathological Journal Gambling", Journal of Clinical Psychopharmacology, vol. 25, No. 6, Dec. 2005, pp. 593-596.

Jain, Adesh K., et al., "Bupropion SR vs. Placebo for Weight Loss in Obese Patients with Depressive Symptoms", Obesity Research, vol. 10, No. 10, Oct. 2002, pp. 1049-1056.

\* cited by examiner

METHODS OF PROVIDING WEIGHT LOSS THERAPY IN PATIENTS WITH MAJOR DEPRESSION

RELATED APPLICATION INFORMATION

The present application is a continuation of U.S. application Ser. No. 15/011,120, filed Jan. 29, 2016, which is a continuation of U.S. application Ser. No. 12/987,909, filed Jan. 10, 2011, now U.S. Pat. No. 9,248,123, which claims the benefit of priority to U.S. Provisional Patent Application Ser. No. 61/293,844, filed Jan. 11, 2010, each of which is hereby incorporated by reference in its entirety.

BACKGROUND OF THE INVENTION

Field of the Invention

The present invention relates to methods of providing weight loss therapy, particularly for patients suffering from major depression.

Description of the Related Art

Obesity has been defined in terms of body mass index (BMI). BMI is calculated as weight (kg)/[height (m)]$^2$. According to the guidelines of the U.S. Centers for Disease Control and Prevention (CDC) and the World Health Organization (WHO), for adults over 20 years old, BMI falls into one of the following categories: below 18.5 is considered underweight, 18.5-24.9 is considered normal, 25.0-29.9 is considered overweight, and 30.0 and above is considered obese (World Health Organization. Physical status: The use and interpretation of anthropometry. Geneva, Switzerland: World Health Organization 1995. WHO Technical Report Series).

The diagnosis of mental disorders is typically based on the criteria provided in the Diagnostic and Statistical Manual of Mental Disorders, fourth edition (DSM-IV) (American Psychiatric Association; Diagnostic and Statistical Manual of Mental Disorders, fourth edition (DSM-IV), Washington, D.C., American Psychiatric Press, 1994). Three major categories of depression described in the DSM-IV are major depressive disorder (i.e., unipolar major depression), dysthymic disorder (i.e., dysthymia), and bipolar disorder (i.e., manic-depressive illness). There are also several subtypes of these main categories of depression. For example, atypical depression is a subtype of all three main types of depression that is characterized by the capacity to be cheered up when presented with positive events (see id.).

According to the DSM-IV, the essential feature of major depressive disorder is a period of at least two weeks during which an individual experiences a depressed mood or the loss of interest or pleasure in nearly all activities (see id.). A diagnosis of major depressive disorder also requires at least four additional symptoms that may include changes in appetite or weight; insomnia; psychomotor agitation or retardation; decreased energy level; feelings of worthlessness or guilt; difficulty thinking, concentrating, or making decisions; and recurrent thoughts of death, suicidal ideation, or attempts to commit suicide (see id.).

In contrast, dysthymic disorder is a milder form of depression with symptoms similar to, but less severe than, those of major depressive disorder. Bipolar disorder is characterized by extreme swings in mood between mania and depression, with mania being accompanied by euphoria, grandiosity, increased energy, decreased need for sleep, rapid speech, and risk taking (see id.).

Depression has been linked to obesity, with recent studies identifying a specific link between major depression (i.e., major depressive disorder) and overweight or obesity. Depression has also been linked to emotional eating, which in turn is linked to high BMI. Further, depressed patients are known to exhibit weight gain as a side effect of certain depression therapies.

U.S. Pat. Nos. 7,375,111 and 7,462,626 disclose the combination of naltrexone and bupropion for weight loss therapy. Further, U.S. Pat. No. 5,817,665 discloses examples in which the combination of naltrexone and an antidepressant is used to treat depression in individuals who are also obese or crave sweets. However, a need exists for an effective method for the treatment of overweight or obesity in the difficult to treat population of overweight or obese patients suffering from major depression. A need also exists for an effective method to concurrently treat major depression and overweight or obesity.

SUMMARY OF THE INVENTION

Disclosed herein are methods of providing weight loss therapy, particularly for patients suffering from major depression. In some embodiments, the methods unexpectedly provide the same amount of weight loss in overweight or obese patients who are suffering from major depression as in overweight or obese patients who are not suffering from major depression. In some embodiments, the dosages of naltrexone and bupropion unexpectedly treat both overweight or obesity and major depression.

In some embodiments, a method for providing weight loss therapy to a patient is provided, comprising: identifying a patient suffering from major depressive disorder, where the patient is also overweight or obese; and reducing weight of the patient by administering to the patient naltrexone or a pharmaceutically acceptable salt thereof and bupropion or a pharmaceutically acceptable salt thereof, where the naltrexone or pharmaceutically acceptable salt thereof is in an amount effective to enhance the weight loss activity of the bupropion or pharmaceutically acceptable salt thereof. In certain embodiments, the method further comprises reducing symptoms of depression in the patient. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m$^2$ or above. In certain embodiments, the patient has a body mass index of 30 kg/m$^2$ or above. In certain embodiments, the patient is overweight. In certain embodiments, the patient is obese. In certain embodiments, the patient is female. In certain embodiments, the weight-loss inducing combination is administered at least once per day. In certain embodiments, the weight-loss inducing combination is administered more than once per day. In certain embodiments, the weight-loss inducing combination is administered for a period of at least 12 weeks. In certain embodiments, the weight-loss inducing combination is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

In some embodiments, a method for providing weight loss therapy to a patient is provided, comprising: identifying a patient suffering from major depressive disorder, wherein the patient is also overweight or obese; and reducing weight of the patient by administering to the patient naltrexone or a pharmaceutically acceptable salt thereof and bupropion or a pharmaceutically acceptable salt thereof, where the amount of the naltrexone or pharmaceutically acceptable salt thereof is about 32 mg per day; where the amount of the bupropion or pharmaceutically acceptable salt thereof is about 360 mg per day; and where each of the naltrexone or pharmaceutically acceptable salt thereof and bupropion or pharmaceutically acceptable salt thereof is in a sustained release formulation.

In some embodiments, a method for selecting a weight loss therapy from among available weight loss therapies is provided, comprising: evaluating a patient to asses whether the patient is simultaneously in need of weight loss therapy and depression therapy; and if so, providing to the patient an effective weight-loss-inducing and antidepressant combination of bupropion or a pharmaceutically acceptable salt thereof and naltrexone or a pharmaceutically acceptable salt thereof as active ingredients. In certain embodiments, the method further comprises providing printed information to the patient indicating that the combination promotes weight loss and reduces symptoms of depression. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m$^2$ or above. In certain embodiments, the patient has a body mass index of 30 kg/m$^2$ or above. In certain embodiments, the patient is overweight. In certain embodiments, the patient is obese. In certain embodiments, the patient is female. In certain embodiments, the weight-loss-inducing and antidepressant combination is administered at least once per day. In certain embodiments, the weight-loss-inducing and antidepressant combination is administered more than once per day. In certain embodiments, the weight-loss-inducing and antidepressant combination is administered for a period of at least 12 weeks. In certain embodiments, the weight-loss-inducing and antidepressant combination is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

In some embodiments, a method for providing weight loss therapy to a patient is provided, comprising: providing to the patient a drug product comprising an effective weight-loss inducing combination of bupropion or a pharmaceutically acceptable salt thereof and naltrexone or a pharmaceutically acceptable salt thereof as active ingredients; and providing to the patient printed information indicating that in depressed patients, the drug product results in a promotion of weight loss and a reduction of symptoms of depression. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m$^2$ or above. In certain embodiments, the patient has a body mass index of 30 kg/m$^2$ or above. In certain embodiments, the patient is overweight. In certain embodiments, the patient is obese. In certain embodiments, the patient is female. In certain embodiments, the drug product is administered at least once per day. In certain embodiments, the drug product is administered more than once per day. In certain embodiments, the drug product is administered for a period of at least 12 weeks. In certain embodiments, the drug product is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

DETAILED DESCRIPTION OF THE PREFERRED EMBODIMENT

In some embodiments, the method is effective to reduce the symptoms of major depression. In some embodiments, the reduction in symptoms of major depression is measured by a percent change from baseline symptoms before treatment. In some embodiments, the reduction in symptoms of major depression is measured by a change in a Montgomery-Åsberg Depression Rating Scale score. In some embodiments, the reduction in symptoms of major depression is measured by a change in an Inventory of Depressive Symptomatology-Self Report (IDS-SR) score. In some embodiments, the reduction in symptoms of major depression is measured by a change as assessed by the Clinical Global Impressions-Improvement (CGI-I) scale. In some of these embodiments, the reduction in symptoms of major depression is measured by a change in response and/or remission rates of depressive symptoms. In a preferred embodiment, the reduction in symptoms of major depression is at least about 40%. In some embodiments, the reduction in symptoms of major depression is, is about, is at least, is at least about 2%, 5%, 10%, 15%, 20%, 25%, 30%, 35%, 40%, 45%, 50%, 55%, 60%, 65%, 70%, 75%, 80%, 85%, 90%, 95%, or 100%, or a range defined by any two of the preceding values. In some embodiments, a reduction in symptoms of major depression is seen at about 4, 8, 12, 16, 20, 24, 36, 48, or 52 weeks, or a range defined by any two of the preceding values.

In some embodiments, the method is effective to promote weight loss or mitigate weight gain in an overweight or obese individual. In some embodiments, the individual has gained weight as a result of depression and/or as a result of being administered another drug product for the treatment of depression. However, in some embodiments, the cause of the individual's overweight or obesity is unknown. In some embodiments, a method of promoting weight loss or mitigating weight gain and reducing symptoms of major depression is provided. In some embodiments, a method of reducing symptoms of major depression is provided regardless of weight loss or mitigation of weight gain. In some embodiments, a method of promoting weight loss or mitigating weight gain is provided regardless of a reduction in symptoms of major depression.

In some embodiments, the individual has a body mass index (BMI) of at least 25 kg/m$^2$. In some embodiments, the individual has a BMI of at least 30 kg/m$^2$. In some embodiments, the individual has a BMI of at least 40 kg/m$^2$. In some embodiments, the individual has a BMI of less than 25 kg/m$^2$, or develops a BMI less than 25 kg/m$^2$ during the course of administration of naltrexone and bupropion. In these embodiments, it may be beneficial for health or cosmetic purposes to mitigate subsequent weight gain or to promote weight loss, thereby reducing the BMI even further. In some embodiments, the individual has been diagnosed by a physician as being overweight or obese. In some embodiments, the individual is identified, including self-identified, as overweight or obese, or is identified as having been diagnosed as overweight or obese.

In some embodiments, the promotion of weight loss is measured by a percent change from a baseline body weight. In some of these embodiments, the amount of weight loss is, is about, is at least, is at least about 0.5%, 1%, 1.5%, 2%, 2.5%, 3%, 4%, 5%, 6%, 7%, 8%, 9%, 10%, 12%, 15%, or more of initial body weight, or a range defined by any two of the preceding values. In some embodiments, the promotion of weight loss is measured as a reduction in weight gain relative to the amount of weight gain experienced when neither or only one of naltrexone and bupropion is administered, and the amount of reduction in weight gain is, is about, is at least, is at least about, 2%, 5%, 10%, 15%, 20%, 25%, 30% 40%, 50%, 60%, 70%, 80%, 90%, 100%, 105%, 110%, 115%, 120%, or more, or a range defined by any two of the preceding values.

In some embodiments, the mitigation of weight gain is measured by a percent change from a baseline body weight. In some of these embodiments, the amount of weight gain is, is about, is not more than, is not more than about 0%, 0.5%, 1%, 1.5%, 2%, 2.5%, 3%, 4%, 5%, 6%, 7%, 8%, 9%, 10% or more of initial body weight, or a range defined by any two of the preceding values.

In some embodiments, the dosage is adjusted so that the patient loses weight at a rate of about 3% of baseline body weight every six months. However, the rate of weight loss for a patient may be adjusted by the treating physician based on the patient's particular needs. In some embodiments, the dosage is adjusted so that the patient exhibits a 50% reduction in symptoms of depression every six months. However, the rate of reduction in symptoms of depression for a patient may also be adjusted by the treating physician based on the patient's particular needs.

In some embodiments, the mitigation of weight gain or promotion of weight loss occurs by increasing satiety in the individual. In some embodiments, the mitigation of weight gain or promotion of weight loss occurs by suppressing the appetite of the individual. In some embodiments, the individual receives depression or weight loss counseling, or both. In some embodiments, the method further comprises instituting a regimen of diet and/or increased activity. In some embodiments, the individual is co-administered another drug product for the treatment of depression. For example, in some embodiments, the individual is co-administered venlafaxine, duloxetine, or aripiprazole.

In some embodiments, treatment of an obese person undergoing or about to begin a period of treatment for depression results in greater mitigation of weight gain or promotion of weight loss than that observed when treating an overweight or normal weight person undergoing or about to begin treatment for depression. In some embodiments, treatment of an obese person undergoing or about to begin a period of treatment for depression results in greater mitigation of weight gain or promotion of weight loss than that observed when treating an obese or overweight person not suffering from depression with bupropion and naltrexone.

In some embodiments, treatment of an overweight person undergoing or about to begin a period of treatment for depression results in greater mitigation of weight gain or promotion of weight loss than that observed when treating an obese or normal weight person undergoing or about to begin treatment for depression. In some embodiments, treatment of an overweight person undergoing or about to begin a treatment for depression results in greater mitigation of weight gain or promotion of weight loss than that observed when treating an obese or overweight person not suffering from depression with bupropion and naltrexone.

In some embodiments, the treatment works as well or better for treating obesity or overweight in an obese or overweight person suffering from major depression as it does for an obese, overweight, or normal weight person not suffering from major depression. For example, in some embodiments, the treatment results in the same weight loss in an obese or overweight person suffering from depression as it would in an obese or overweight person not suffering from depression. In some embodiments, the treatment results in greater weight loss in an obese or overweight person suffering from depression as it would in an obese or overweight person not suffering from depression.

In some embodiments, the treatment works as well or better for treating depression in an obese or overweight person suffering from major depression as it does for a normal weight person suffering from major depression. For example, in some embodiments, the treatment results in the same reduction in symptoms of depression for an obese or overweight person as it would in a normal weight person. In some embodiments, the treatment results in a greater reduction in the symptoms of depression in an obese or overweight person suffering from depression as it would in a normal weight person suffering from depression.

In some embodiments, naltrexone and bupropion are each administered once per day. In some embodiments, naltrexone and bupropion are each divided into equal doses and administered more than once per day. In some embodiments, naltrexone and bupropion are each divided into unequal doses and administered more than once per day. In some embodiments, naltrexone and bupropion are divided into a different number of doses and are administered a different number of times per day. In one such embodiment, the dose of one of naltrexone or bupropion is divided, while the dose of the other is not.

In some embodiments, one or both of naltrexone and bupropion is administered one, two, three, four, or more times per day. In some embodiments, one or both of naltrexone and bupropion are administered in a controlled release formulation. Either or both compounds can be administered less than once per day, for example once every 2, 3, 4, 5, 6, 7, 8, 9, 10, 11, 12, 13, or 14 days, or every 1 or 2 weeks, or a range defined by any two of the preceding values.

The exact formulation, route of administration, and dosage for naltrexone and bupropion combinations described herein can be chosen by the individual physician in view of the patient's condition. (See e.g., Fingl et al. 1975, in "The Pharmacological Basis of Therapeutics," Ch. 1 p. 1). In some embodiments, the daily dose of naltrexone and bupropion is the same, and in some embodiments, the daily dose is different.

In some embodiments, the daily dose of naltrexone can range from about 4 mg to about 50 mg, or about 4 mg to about 32 mg, or about 8 mg to about 32 mg, or about 8 mg to about 16 mg. In some embodiments, the daily dose is about 4 mg, about 8 mg, about 12 mg, about 16 mg, about 32 mg, or about 48 mg of naltrexone, or a range defined by any two of the preceding values. In some embodiments, the daily dose is administered in a single oral dosage form. The selection of a particular dosage may be based on the weight of the patient. The selection of a particular dosage may be based on the identity, dosage, and/or dosing schedule of another co-administered compound. However, in some embodiments, it may be necessary to use dosages outside these ranges.

In some embodiments, the daily dose of bupropion can range from about 30 mg to about 500 mg, or about 30 mg to about 360 mg, or about 90 mg to about 360 mg. In some embodiments, the daily dose is about 30 mg, about 90 mg, about 180 mg, about 360 mg, or about 450 mg of bupropion, or a range defined by any two of the preceding values. In some embodiments, the daily dose is administered in a single oral dosage form. The selection of a particular dosage may be based on the weight of the patient. The selection of a particular dosage may be based on the identity, dosage and/or dosing schedule of another co-administered compound. However, in some embodiments, it may be necessary to use dosages outside these ranges.

In some embodiments, at least one of naltrexone and bupropion is administered with varying frequency during treatment. In some of these embodiments, the varying frequency comprises a decreased frequency over time. For example, one or both of naltrexone and bupropion can be initially administered more than once per day, followed by administration only once per day at a later point in treatment. In some embodiments, the daily dosage of at least one of naltrexone and bupropion is consistent despite the varying frequency of administration. For example, in some embodiments, two tablets of each of naltrexone and bupropion are initially administered twice per day, while four tablets of each of naltrexone and bupropion are administered once per day at a later point in treatment. Alternatively, in some embodiments, one or two tablets of each of naltrexone and bupropion are administered at a later point in treatment, where the one or two tablets have an equivalent total daily dosage as the two tablets each of naltrexone and bupropion initially administered twice per day.

In some embodiments where one or both of naltrexone and bupropion are administered less than once per day in a controlled release or sustained release (SR) formulation, the dose is selected so that the patient receives a daily dose that is about the same as a daily dose described herein.

In some embodiments, at least one of naltrexone or bupropion is administered in consistent daily dosages throughout the period of treatment. In some embodiments, at least one of naltrexone or bupropion is administered in varying daily dosages during the period of treatment. In some of these embodiments, the daily dosages comprise increasing daily dosages over time. In some of these embodiments, the daily dosages comprise decreasing daily dosages over time.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is in a sustained release or controlled release formulation. For example, sustained release forms of naltrexone are described in U.S. Patent Publication No. 2007/0281021, which is incorporated herein by reference in its entirety and for all purposes, including without limitation for the purpose of describing sustained release forms of naltrexone and bupropion, methods of making and formulating them into suitable dosage forms, and methods of administering them. In some embodiments, at least one of naltrexone or bupropion is administered with a physiologically acceptable carrier, diluent, or excipient, or a combination thereof. Non-limiting examples of naltrexone/bupropion combinations, formulations thereof, and methods of administering them are disclosed in U.S. Pat. Nos. 7,375,111 and 7,462,626, both of which are incorporated herein by reference in their entirety and for all purposes, including without limitation for the purpose of describing combinations of naltrexone and bupropion, methods of making and formulating them into suitable dosage forms, and methods of administering them. Reference herein to the use or administration of naltrexone/bupropion combinations will be understood to include all modes of administration disclosed or referred to herein, including without limitation separate administration, administration in a single dosage form, administration in the form of salts, prodrugs and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to the bupropion. In some embodiments, naltrexone is administered subsequent to the bupropion. In some embodiments, naltrexone and the bupropion are co-administered. As used herein, co-administration includes administration in a single dosage form, or separate dosage forms that are administered at, or nearly at, the same time.

In some embodiments, the administration of naltrexone and bupropion is continued for a period of, or of about, 4, 12, 16, 20, 24, 36, 48, or 52 weeks, or a range defined by any two of the preceding values. In some embodiments, the administration of naltrexone and bupropion is continued until the reduction in symptoms of depression is stabilized for a period of, or of about, 1, 2, 3, 4, 5, 6, or more weeks, or a range defined by any two of the preceding values. In some embodiments, the administration of naltrexone and bupropion is continued until the mitigation of weight gain or promotion of weight loss is stabilized for a period of, or of about, 1, 2, 3, 4, 5, 6, or more weeks, or a range defined by any two of the preceding values. In some embodiments, administration of naltrexone and bupropion is continued until the individual no longer needs treatment for major depressive disorder. In some embodiments, administration of naltrexone and bupropion is continued until the individual no longer needs treatment for obesity or overweight.

The compositions described herein may, if desired, be presented in a pack or dispenser device which may contain one or more unit dosage forms containing one or both of the active ingredients. The pack may, for example, comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Non-limiting examples of packs and dispensers as well as oral dosage forms are disclosed in U.S. Patent Publication Nos. 2008-0110792 and 2008-0113026, both of which are hereby incorporated herein by reference in their entirety and for all purposes, including without limitation for the purpose of describing combinations of naltrexone and bupropion, methods of making and formulating them into suitable dosage forms, methods of packing and dispensing them, and methods of administering them.

In some embodiments, the single oral dosage form comprises a plurality of layers. For example, in some embodiments, the single oral dosage form is a trilayer tablet with a first pharmaceutical layer, a second pharmaceutical layer, and an intermediate layer disposed between the first and second pharmaceutical layers that is configured to rapidly dissolve in vivo. Non-limiting examples of multilayer tablets are disclosed in U.S. Patent Application Nos. 2008-0110792 and 2008-0113026, both of which are hereby incorporated herein by reference in their entirety and for all purposes.

Instructions and/or information may be present in a variety of forms, including printed information on a suitable medium or substrate (e.g., a piece or pieces of paper on which the information is printed), computer readable medium (e.g., diskette, CD, etc., on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver involved in treatment of the patient.

Throughout the present disclosure, when a particular compound is mentioned by name, for example, bupropion or naltrexone, it is understood that the scope of the present disclosure encompasses pharmaceutically acceptable salts, esters, amides, metabolites, or prodrugs of the named compound. For example, in any of the embodiments herein, an active metabolite of naltrexone, e.g., 6-β naltrexol, can be used in combination with, or instead of, naltrexone. In any of the embodiments herein, an active metabolite of bupropion, including S,S-hydroxybupropion (i.e., radafaxine), can be used in combination with, or instead of, bupropion.

As used herein, "mitigate" or "mitigation" of weight gain includes preventing or decreasing the amount of weight gain associated with depression or with the administration of another drug therapy for depression. In some embodiments, mitigation is measured relative to the amount of weight gain typically experienced when only one or neither of naltrexone or bupropion is administered.

As used herein, "promotion" of weight loss includes causing weight loss relative to a baseline weight for a least a portion of the period of treatment. This includes an individual that initially gains some weight, but during the course of treatment loses weight relative to a baseline prior to beginning treatment, as well as individuals that regain a portion or all of the weight that is lost by the end of the treatment period. In a preferred embodiment, at the end of the treatment period, the individual has lost weight relative to a baseline. In a preferred embodiment, mitigation of weight gain or promotion of weight loss in a patient administered naltrexone and bupropion is greater than when neither or only one of naltrexone or bupropion is administered, and more preferably an at least additive, or better than additive, or synergistic, effect of administering the two compounds is achieved.

The term "pharmaceutically acceptable salt" refers to a formulation of a compound that does not cause significant irritation to an organism to which it is administered and does not abrogate the biological activity and properties of the compound. Pharmaceutical salts can be obtained by routine experimentation. Non-limiting examples of pharmaceutically acceptable salts include bupropion hydrochloride, radafaxine hydrochloride, naltrexone hydrochloride, and 6-β naltrexol hydrochloride.

A "prodrug" refers to an agent that is converted into the parent drug in vivo. Prodrugs are often useful because, in some situations, they may be easier to administer than the parent drug. They may, for instance, be bioavailable by oral administration to a greater extent than the parent. The prodrug may also have improved solubility in pharmaceutical compositions over the parent drug, demonstrate increased palatability, or be easier to formulate. Non-limiting examples of suitable prodrugs include those described in U.S. Patent Publication No. 2007/0117827, which is incorporated herein by reference in its entirety and for all purposes, including without limitation for the purposes of describing naltrexone metabolites and prodrugs thereof, methods of making and formulating them into suitable dosage forms, and methods of administering them.

It will be understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLES

The examples below are non-limiting and are merely representative of various aspects of the invention.

Example 1: Naltrexone and Bupropion

A 24-week open label study of sustained release naltrexone (naltrexone SR) plus sustained release bupropion (bupropion SR) for depression and minimization of weight gain in subjects with BMI ≥27 and ≤43 kg/m$^2$ was performed according to the dose escalation schedule provided in Table 1. All subjects met the DSM-IV criteria for major depression (without psychotic features) and had an IDS-SR total score ≥26.

TABLE 1

|  | Morning Dose | Evening Dose | Total Daily Dose |
| --- | --- | --- | --- |
| Week 1 | one tablet (8 mg naltrexone SR + 90 mg bupropion SR/tablet) | — | 8 mg naltrexone SR/90 mg bupropion SR |
| Week 2 | one tablet (8 mg naltrexone SR + 90 mg bupropion SR/tablet) | one tablet (8 mg naltrexone SR + 90 mg bupropion SR/tablet) | 16 mg naltrexone SR/180 mg bupropion SR |
| Week 3 | two tablets (8 mg naltrexone SR + 90 mg bupropion SR/tablet) | one tablet (8 mg naltrexone SR + 90 mg bupropion SR/tablet) | 24 mg naltrexone SR/270 mg bupropion SR |
| Week 4 - Onward | two tablets (8 mg naltrexone SR + 90 mg bupropion SR/tablet) | two tablets (8 mg naltrexone SR + 90 mg bupropion SR/tablet) | 32 mg naltrexone SR/360 mg bupropion SR |

The primary outcomes were percent and absolute change from baseline in total body weight and subject-reported depression at weeks 12 and 24. Other efficacy measures were: change in waist circumference; serum leptin and ghrelin levels; creatinine levels; and safety and tolerability. Adverse events and vital signs (e.g., systolic and diastolic blood pressure and pulse) were used to monitor safety and tolerability. Of the 25 subjects enrolled, all were female, 23 were Caucasian, and the average age was 47. All 25 subjects provided at least one post-baseline evaluation, and 14 and 12 of the subjects completed 12 and 24 weeks of treatment, respectively.

MADRS total scores decreased from 23.65 to 10.52 and 8.35 at weeks 12 and 24, respectively. IDS-SR total scores decreased from 43.20 to about 23 and 16 at weeks 12 and 24, respectively. CGI-I response rates were 90.0% and 95.0% at weeks 12 and 24, respectively, as measured by full analysis set, last observation carried forward (FAS LOCF). CGI-I remission rates were 55.0% and 70.0% at weeks 12 and 24, respectively, as measured by FAS LOCF. Total body weight decreased by 4.42% and 5.86% at weeks 12 and 24, respectively, as measured by FAS LOCF, and 6.75% and 9.96% at weeks 12 and 24, respectively, as measured by observed case (OC) analysis. The most common adverse events were nausea, constipation, headache, insomnia, dizziness, and hot flush. In overweight or obese subjects, naltrexone plus bupropion reduced symptoms of depression while preventing weight gain.

Example 2: Naltrexone and Bupropion

Patients having a BMI of greater than 25 are identified. Each patient is instructed to take two 8 mg tablets of naltrexone (SR) twice daily, in addition to two 90 mg tablets of bupropion (SR) twice daily.

The patients are monitored for a period of months. It is recommended that the dosage be adjusted so that each patient loses weight at a rate of at least about 3% of initial weight and exhibits a 50% reduction in symptoms of depression every six months. However, the rate of weight loss and reduction in symptoms of depression for each patient may be adjusted by the treating physician based on the patient's particular needs.

If the initial dosage is not effective, then the dosage of either or both of naltrexone and bupropion can be increased. Alternatively, if the initial dosage results in a more rapid weight loss or reduction in symptoms of depression than the above rates, the dosage of either or both of naltrexone and bupropion can be reduced.

Example 3: Naltrexone and Bupropion

In a multicenter, randomized, blinded, placebo-controlled clinical trial, the following drug combinations are tested:

Group 1—naltrexone (SR) 16 mg po BID+bupropion (SR) 180 mg po BID

Group 2—N-placebo po BID+bupropion (SR) 180 mg po BID

Group 3—P-placebo po BID+naltrexone (SR) 16 mg po BID

Group 4—N-placebo po BID+P-placebo po BID.

In any of the above groups, the dosage of naltrexone may be administered in doses in the range between 5 mg and 50 mg, for example, 5 mg, 10 mg, 15 mg, 20 mg, 25 mg, 30 mg, 35 mg, 40 mg, 45 mg, and 50 mg. In any of the above groups, the dosage of bupropion may be administered in doses in the range between 30 mg and 500 mg, for example, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, and 500 mg.

The primary endpoints are percent and absolute change from baseline in total body weight and subject-reported depression at weeks 12 and 24. Secondary endpoints include percent and absolute change from baseline in total body weight at weeks 36 and 48, change in waist circumference; serum leptin and ghrelin levels; creatinine levels; and safety and tolerability. Adverse events, laboratory parameters, and vital signs are used to monitor safety and tolerability.

What is claimed is:

1. A method for providing weight loss therapy to an overweight or obese patient suffering from major depressive disorder, comprising administering to the patient an amount of naltrexone or a pharmaceutically acceptable salt thereof in a range of about 4 mg to about 50 mg per day and an amount of bupropion or a pharmaceutically acceptable salt thereof in a range of about 30 mg to about 500 mg per day;
  wherein said method provides about the same amount of weight loss in overweight or obese patients who are suffering from major depressive disorder as in overweight or obese patients who are not suffering from major depressive disorder.

2. The method of claim 1, wherein the method provides a reduction in symptoms of depression in the patient.

3. The method of claim 1, wherein the patient is overweight.

4. The method of claim 1, wherein the patient is obese.

5. The method of claim 1, wherein the naltrexone or a pharmaceutically acceptable salt thereof and bupropion or a pharmaceutically acceptable salt thereof is administered once per day.

6. The method of claim 1, wherein the naltrexone or a pharmaceutically acceptable salt thereof and bupropion or a pharmaceutically acceptable salt thereof is administered more than once per day.

7. The method of claim 1, wherein the naltrexone or pharmaceutically acceptable salt thereof is administered prior to or subsequent to the bupropion or pharmaceutically acceptable salt thereof.

8. The method of claim 1, wherein the naltrexone or pharmaceutically acceptable salt thereof and the bupropion or pharmaceutically acceptable salt thereof are in a single oral dosage form.

9. The method of claim 8, wherein the single oral dosage form further comprises a pharmaceutically acceptable excipient, diluent, or carrier.

10. The method of claim 1, wherein the amount of naltrexone or pharmaceutically acceptable salt thereof is about 16 mg or about 32 mg per day; and wherein the amount of bupropion or pharmaceutically acceptable salt thereof is about 360 mg per day.

11. The method of claim 1, wherein the initial daily dose administered to the patient is about 4 mg or about 8 mg of the naltrexone or pharmaceutically acceptable salt thereof and about 90 mg of the bupropion or pharmaceutically acceptable salt thereof; and wherein the daily dose administered to the patient for maintenance is about 16 mg or about 32 mg of the naltrexone or pharmaceutically acceptable salt thereof and about 360 mg of the bupropion or pharmaceutically acceptable salt thereof.

12. The method of claim 1, wherein the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and wherein the daily dose of the bupropion or pharmaceutically acceptable salt thereof is escalated from 90 mg in week one to 180 mg in week two, 270 mg in week three, and 360 mg in week four and thereafter.

13. The method of claim 12, wherein at least one of the naltrexone or pharmaceutically acceptable salt thereof and bupropion or pharmaceutically acceptable salt thereof is in a sustained release formulation.

14. The method of claim 13, wherein the naltrexone or pharmaceutically acceptable salt thereof and the bupropion or pharmaceutically acceptable salt thereof are in a single oral dosage form.

15. The method of claim 12, wherein each of the naltrexone or pharmaceutically acceptable salt thereof and bupropion or pharmaceutically acceptable salt thereof is in a sustained release formulation.

16. The method of claim 15, wherein the naltrexone or pharmaceutically acceptable salt thereof and the bupropion or pharmaceutically acceptable salt thereof are in a single oral dosage form.

17. The method of claim 1, wherein at least one of the naltrexone or pharmaceutically acceptable salt thereof and bupropion or pharmaceutically acceptable salt thereof is in a sustained release formulation.

18. The method of claim 1, wherein each of the naltrexone or pharmaceutically acceptable salt thereof and bupropion or pharmaceutically acceptable salt thereof is in a sustained release formulation.

19. A method for providing weight loss therapy to an overweight or obese patient suffering from major depressive disorder, comprising administering to the patient an amount of naltrexone or a pharmaceutically acceptable salt thereof and an amount of bupropion or a pharmaceutically acceptable salt thereof, wherein the amount of naltrexone or pharmaceutically acceptable salt thereof is about 32 mg per day; wherein the amount of bupropion or pharmaceutically acceptable salt thereof is about 360 mg per day;
  wherein each of naltrexone or pharmaceutically acceptable salt thereof and bupropion or pharmaceutically acceptable salt thereof is in a sustained release formulation, and said method provides about the same amount of weight loss in overweight or obese patients who are suffering from major depressive disorder as in overweight or obese patients who are not suffering from major depressive disorder.

* * * * *